US00PP33925P3

(12) United States Plant Patent
Schoone

(10) Patent No.: US PP33,925 P3
(45) Date of Patent: Feb. 1, 2022

(54) ***PHALAENOPSIS* PLANT NAMED 'SECRET MESSAGES'**

(50) Latin Name: *Phalaenopsis hybrida*
Varietal Denomination: Secret Messages

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,966

(22) Filed: Jun. 5, 2021

(65) Prior Publication Data

US 2021/0385992 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Secret Messages', characterized by its upright plant habit; moderately vigorous to vigorous growth habit; strong flowering stems; strong leaves; freely flowering habit with typically two inflorescences per plant, each inflorescence with numerous flowers; large white-colored flowers with variable dark purple-colored dashes and spots radiating from the center of the flower; and good postproduction longevity.

2 Drawing Sheets

Figure 1:
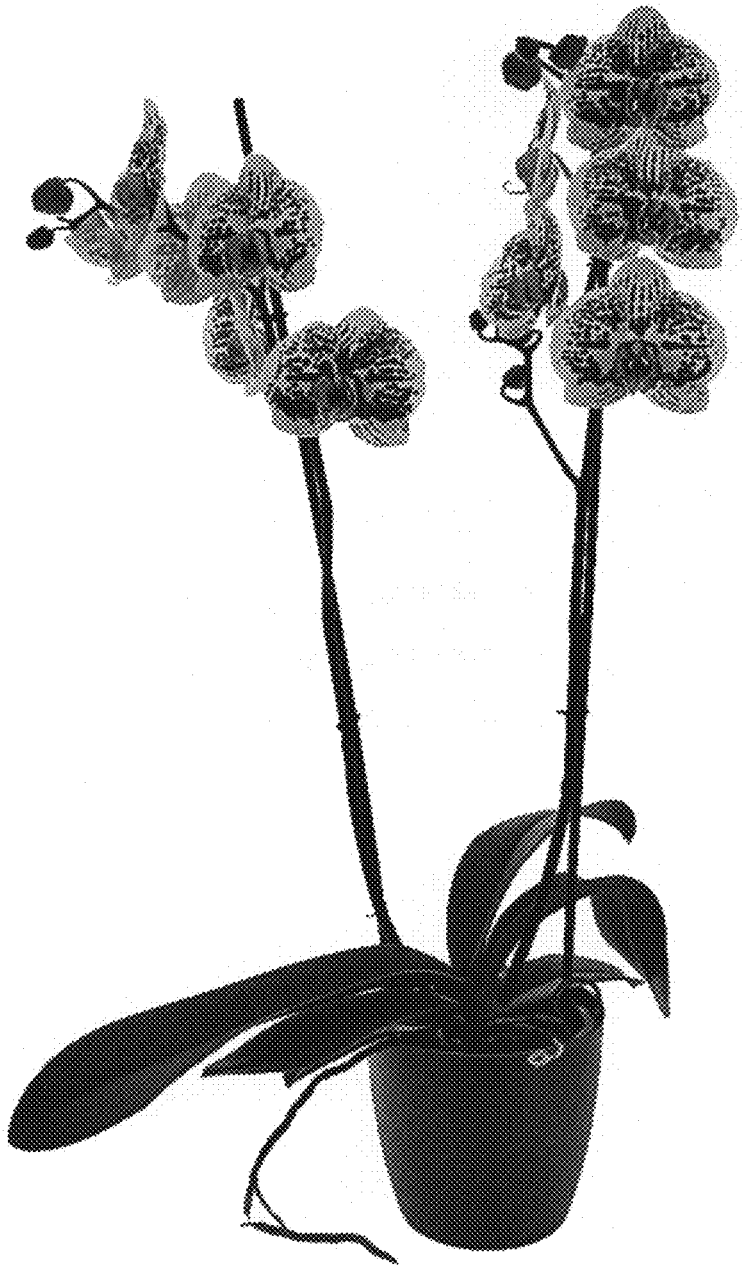

Botanical designation: *Phalaenopsis hybrida.*
Cultivar denomination: 'SECRET MESSAGES'.

CROSS-REFERENCED TO CLOSELY-RELATED APPLICATIONS

Title: Varieties of *Phalaenopsis* Plants
Inventor: René Schoone
Filed: Jun. 6, 2020
Ser. No. 62/705,003
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Apr. 23, 2020, application number 2020/1107. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Secret Messages'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in June, 2011 in Nantou, Taiwan of *Phalaenopsis hybrida* 'Chiada Laura', not patented, as the female, or seed, parent with *Phalaenopsis hybrida* 'Lawrence of Arabia', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in June, 2017.

Asexual reproduction of the new *Phalaenopsis* plant by in vitro meristem propagation in a controlled environment in Assendelft, The Netherlands since June, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Secret Messages'. These characteristics in combination distinguish 'Secret Messages' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Large white-colored flowers with variable dark purple-colored dashes and spots radiating from the center of the flower.
7. Good postproduction longevity.

Plants of the new *Phalaenopsis* can be compared to plants of the female parent, 'Chiada Laura'. Plants of the new *Phalaenopsis* differ primarily from plants of 'Chiada Laura' in flower color as plants of the new *Phalaenopsis* have white-colored flowers with dark purple-colored dashes and spots radiating from the center of the flower whereas plants of 'Chiada Laura' have yellow-colored flowers without spots.

Plants of the new *Phalaenopsis* can be compared to plants of the male parent, 'Lawrence of Arabia'. Plants of the new *Phalaenopsis* differ primarily from plants of 'Lawrence of Arabia' in flower color as plants of the new *Phalaenopsis* have white-colored flowers with dark purple-colored dashes and spots radiating from the center of the flower whereas plants of 'Lawrence of Arabia' have yellow-colored flowers with more spots than plants of the new *Phalaenopsis*.

Plants of the new *Phalaenopsis* can be compared to plants of *Phalaenopsis hybrida* 'Tropic Ocelot', not patented. In side-by-side comparisons, plants of the new *Phalaenopsis* differ primarily from plants of 'Tropic Ocelot' in flower color as flowers of plants of the new *Phalaenopsis* have fewer spots than flowers of plants of 'Tropic Ocelot'. In addition, petals of plants of the new *Phalaenopsis* are incurved whereas petals of plants of 'Tropic Ocelot' are recurved.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Secret Messages' grown in a container.

Figure 2:
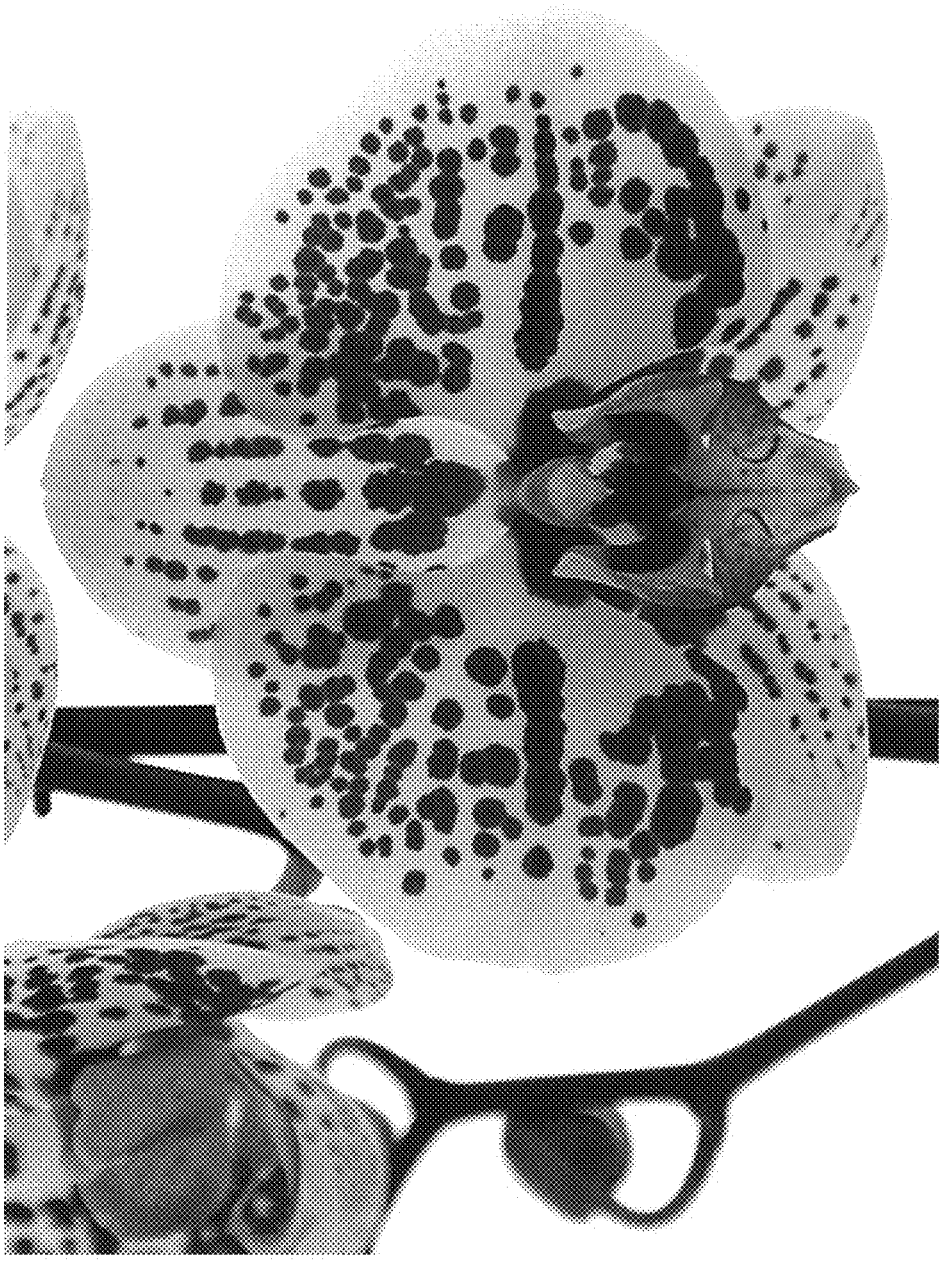

The photograph on the second sheet (FIG. 2) is a close-up view of a typical flower of 'Secret Messages'.

DETAILED BOTANICAL DESCRIPTION

The aforementioned photographs and following observations and measurements describe plants grown during the summer in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Secret Messages'.

Parentage:

*Female parent.*—*Phalaenopsis hybrida* 'Chiada Laura', not patented.

*Male parent.*—*Phalaenopsis hybrida* 'Lawrence of Arabia', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane.*—About 11.8 cm.

*Plant height, substrate level to top of inflorescences.*—About 53.9 cm.

*Plant diameter or spread.*—About 35.1 cm.

Leaf description:

*Arrangement and quantity.*—Distichous, simple; sessile; about six leaves per plant.

*Length.*—About 23 cm.

*Width.*—About 6.1 cm.

*Aspect.*—Upright to outwardly arching.

*Shape.*—Narrowly obovate; slightly concave and moderately carinate.

*Apex.*—Unequal broadly acute.

*Base.*—Sheathing. Sheath length: About 1.9 cm. Sheath width: About 1.4 cm. Sheath color: Close to 144A.

*Margin.*—Entire; not undulate.

*Texture and luster, upper and lower surfaces.*—Smooth, glabrous; slightly to moderately glossy.

*Venation pattern.*—Camptodromous.

*Color.*—Developing leaves, upper surface: Close to between NN137A and 147A. Developing leaves, lower surface: Close to 146A. Fully expanded leaves, upper surface: Close to between NN137A and 147A; venation, close to NN137A. Fully expanded leaves, lower surface: Slightly darker than between 143A and 146A; venation, close to 144A.

Inflorescence description:

*Appearance and flowering habit*.—Showy zygomorphic flowers arranged on axillary branched racemes; typically two inflorescences per plant; each inflorescence with about ten flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about four weeks on the plant; flowers not persistent.

*Inflorescence length* (*lowermost flower to inflorescence apex*).—About 27.5 cm.

*Inflorescence width*.—About 14.5 cm.

*Flower buds*.—Height: About 1.8 cm. Diameter: About 1.4 cm by 1.6 cm. Shape: Broadly ovate. Color: Close to 145A; towards the apex, close to 152D and slightly tinged with close to N77B; venation, close to 200A.

*Flower size*.—Large, about 8.2 cm (vertical) by 9.1 cm (horizontal).

*Flower depth*.—About 3.2 cm.

*Petals, quantity and arrangement*.—Three, two lateral petals and one center petal transformed into a labellum.

*Lateral petals*.—Length: About 4.3 cm. Width: About 5.7 cm. Shape: Lunate to reniform. Apex: Shallowly retuse. Margin: Entire. Texture and luster, upper and lower surfaces: Smooth, glabrous, velvety; matte. Color: When opening, upper surface: Close to NN155C with variable dashes and spots, close to 59A and 187C to darker than 187C, radiating from the center of the flower; towards the base, close to 59A to darker than 59A. When opening, lower surface: Close to NN155C; variable dashes and spots from the upper surface visible, close to N77D to lighter than N77D. Fully opened, upper surface: Close to NN155D with variable dashes and spots, close to 59A, N79C and 187C to slightly darker than 187C, radiating from the center of the flower; towards the base, close to between 59A and N79C; color does not change with subsequent development. Fully opened, lower surface: Close to NN155D; variable dashes and spots from the upper surface visible, close to N77D to lighter than N77D; color does not change with subsequent development.

*Labella*.—Appearance: Three-parted with two lateral lobes and a central lobe. Length, lateral lobes: About 2 cm. Width, lateral lobes: About 1.5 cm. Length, central lobe: About 3.6 cm. Width, central lobe: About 8 mm to 23 mm. Shape, lateral lobes: Obovate. Shape, central lobe: Deltoid. Apex, lateral lobes: Retuse. Apex, central lobe: Cleft with two narrow and strongly recurved cirrose tips, about 1.1 cm in length and about 1.3 mm in width. Margins, lateral lobes: Entire; slightly undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 5 mm in width and about 7 mm in height. Color: When opening, upper surface: Lateral lobes: Close to NN155D; lower half, close to 154B; large central blotch, close to 187B to 187C; venation, distally, close to N80B. Central lobe: Ground color, close to 155B; upper half, close to 160A to 160B; lower half, close to 76C with stripes, close to NN74B to NN74C; at the base (at column connection), close to 187B; cirrose tips, close to 155B with dots, close to 59A. Callosities: Close to 200A; towards the base, close to 2D. When opening, lower surface: Lateral lobes: Close to 76C; central blotch visible from upper surface, close to 201D; lower half, close to 154B; towards the base, close to NN155C; towards the margins, close to 185D. Central lobe: Close to N155A; upper half, close to between 154B and 160C; towards the margins, close to 60C to 60D and at the edges, close to 59A; cirrose tips, close to 155B with dots, close to 59A. Fully opened, upper surface: Lateral lobes: Close to NN155D; lower half, close to 2A; large central blotch, close to 187C; venation, distally, close to N80B. Central lobe: Ground color, close to 155B; upper half, close to 160C; lower half with stripes, close to NN74B to NN74C; at the base (at column connection), close to 187B; cirrose tips, close to 155B with dots, close to 59A. Callosities: Close to 200A; towards the base, close to 2D. Fully opened, lower surface: Lateral lobes: Close to 76C; central blotch visible from upper surface, close to 201D; lower half, close to 154B; towards the base, close to NN155C; towards the margins, close to 185D. Central lobe: Close to N155A; upper half, close to between 154B and 160C; towards the margins, close to 60C to 60D and at the edges, close to 59A; cirrose tips, close to 155B with dots, close to 59A.

*Sepals*.—Quantity and arrangement: Three, one upper dorsal sepal and two lower lateral sepals. Length, dorsal sepal: About 4.5 cm. Width, dorsal sepal: About 3.5 cm. Length, lateral sepals: About 4.6 cm. Width, lateral sepals: About 3.2 cm. Shape, dorsal sepal: Broadly elliptic to slightly obovate. Shape, lateral sepals: Ovate. Apex, dorsal sepal: Obtuse. Apex, lateral sepals: Bluntly acute. Base, dorsal and lateral sepals: Cuneate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to NN155D with variable dashes and spots, close to 59A and 187C to darker than 187C, radiating from the center of the flower; towards the base, close to N78A. When opening, lower surface: Close to 156C; towards the margins and apex, close to 157D; variable dashes and spots from the upper surface visible, close to N77D to lighter than N77D. Fully opened, upper surface: Close to NN155D with variable dashes and spots, close to 59A, N79C and 187C to slightly darker than 187C, radiating from the center of the flower; towards the base, close to between 59A and N79C; color does not change with subsequent development. Fully opened, lower surface: Close to 76C and 76D to lighter than 76D; towards the margins and apex, close to NN155A; towards the base, close to 155C: variable dashes and spots from the upper surface visible, close to N77B to N77D to lighter than N77D; color does not change with subsequent development. Color, lateral sepals: When opening, upper surface: Close to 155C; towards the margins and base, close to 157D; variable dashes and spots, close to 59A and 187C to darker than 187C, radiating from the center of the flower; towards the base, close to 59A to darker than 59A. When opening, lower surface: Close to 157A; towards the margins and apex, close to 157D; towards the base, close to 195A; variable dashes and spots from the upper surface visible, close to N77B to N77D to lighter than N77D. Fully opened, upper surface: Close to NN155D with variable dashes and spots, close to 59A, N79C and 187C to slightly darker than 187C, radiating from the center of the flower; towards the base, close to between 59A and N79C; color does not change with subsequent development. Fully opened, lower surface: Close to 76C to 76D; towards the margins and apex, close to NN155A; towards the base, close to 195B: variable dashes and spots from the upper surface visible, close to N77B to N77D to lighter than N77D; color does not change with subsequent development.

*Peduncles*.—Length: About 55.1 cm. Diameter: About 5.5 mm. Strength: Strong. Aspect: Upright to outwardly arching. Texture and luster: Smooth, glabrous; matte. Color: Darker than between 147A and 197A; proximally, close to between 147A and 202A; fine dots, close to 143A.

*Pedicels*.—Length: About 3.7 cm. Diameter: About 3 mm. Strength: Moderately strong. Aspect: About 65° from peduncle axis. Texture and luster: Smooth, glabrous; matte. Color: Close to 145B; distally, close to N155B and proximally, close to 146D tinged with close to N77B.

*Reproductive organs*.—Androecium: Column length: About 9 mm. Column width: About 6 mm. Column color: Close to 77B; distally, close to N155A. Pollinia quantity: Two. Pollinia diameter (per two pollinia): About 3 mm. Pollinia color: Close to 17A to 17B. Gynoecium: Stigma length: About 3.5 mm. Stigma width: About 5 mm. Stigma shape: Reniform. Stigma color: Close to N155A with margins, close to 77A to 77B. Ovary length: About 8 mm. Ovary diameter: About 1 cm. Ovary color: Close to 145A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Secret Messages' as illustrated and described.

* * * * *